United States Patent [19]

Deeg et al.

[11] 4,438,204
[45] Mar. 20, 1984

[54] DETERMINATION OF GLYCOSILATED HEMOGLOBIN

[75] Inventors: Rolf Deeg, Seeshaupt; Urban Schmitt, Tutzing; Joachim Ziegenhorn, Starnberg, all of Fed. Rep. of Germany

[73] Assignee: Boehringer Mannheim GmbH, Mannheim, Fed. Rep. of Germany

[21] Appl. No.: 426,510

[22] Filed: Sep. 29, 1982

[30] Foreign Application Priority Data

Oct. 16, 1981 [DE] Fed. Rep. of Germany ....... 3141146

[51] Int. Cl.³ ...................... G01N 33/72; G01N 33/66
[52] U.S. Cl. .......................................... 436/67; 436/17
[58] Field of Search ..................................... 436/17, 67

[56] References Cited

U.S. PATENT DOCUMENTS

| | | | |
|---|---|---|---|
| 4,189,304 | 2/1980 | Adams | 422/56 X |
| 4,200,435 | 4/1980 | Stroupe | 436/67 |
| 4,255,385 | 3/1981 | Stroupe | 436/67 X |
| 4,371,374 | 2/1983 | Cerami | 422/56 X |

*Primary Examiner*—Sidney Marantz
*Attorney, Agent, or Firm*—Felfe & Lynch

[57] ABSTRACT

A process for the determination of glycosilated hemoglobin in a blood sample comprises liberating glycosilated and non-glycosilated hemoglobin from the erythrocytes by chemical or physical treatment; converting, if desired, the hemoglobin into methemoglobin, and thereafter differentiating the glycosilated and non-glycosilated hemoglobin portion using its reaction with haptoglobin, and determining the glycosilated and/or the non-glycosilated hemoglobin portion.

The present invention also provides a reagent for the determination of glycosilated hemoglobin in a blood sample, as well as a reagent for the differentiation of glycosilated and non-glycosilated hemoglobin, comprising haptoglobin.

12 Claims, 3 Drawing Figures

DETERMINATION OF GLYCOSILATED HEMOGLOBIN

BACKGROUND

The present invention is concerned with a process and a reagent for the determination of glycosilated hemoglobin in blood samples.

Glycosilated hemoglobin ($HbA_1$) is formed by the non-enzymatic glycosilation of hemoglobin ($HbA_0$). Normally, the concentration of glycosilated hemoglobin in blood is about 5%, referred to the total hemoglobin but, in the case of diabetics, this concentration may be increased 2 to 4 fold.

The determination of the glycosilated portion of the total hemoglobin has, in recent years, achieved importance in the diagnosis of diabetes (cf. L. Jovanovic and C. M. Peterson, Am. J. Med., 70, 331–338/1981). The reaction between individual hemoglobin molecules and glucose gives a stable reaction product which remains intact during the whole life time of the erythrocytes, i.e. about 100 to 200 days. Brief variations of the blood sugar content do not decisively influence the concentration of glycosilated hemoglobin. Therefore, the concentration of glycosilated hemoglobin mirrors relatively exactly the average glucose concentration in the blood of a patient over a long period of time.

Many processes are known for the determination of the glycosilated portion of the total hemoglobin. In clinical laboratories, the most widely used are chromatographic separation processes. The glycosilated portion of the hemoglobin is thereby separated from the non-glycosilated portion with the use of a chromatography column, of a microcolumn or also with the use of HPLC methods (HPLC=high pressure liquid chromatography), the columns being filled with an ion exchanger, for example with Bio Rex 70. However, all these methods are sensitive to changes of the pH value, temperature and ion concentrations. Therefore, the separation processes must be carried out very carefully in order to obtain optimum results (cf. loc. cit., page 332).

Federal Republic of Germany Patent Specification No. 29 50 457 describes a process for the determination of glycosilated hemoglobin in blood samples in which the alteration of the spectroscopic properties of a blood sample brought about by the addition of an allosteric effector is utilised for the determination of the $HbA_1$. Only the non-glycosilated main portion of the hemoglobin is hereby influenced. In the relevant range, the measured extinction differences are very small. Furthermore, they become even smaller when the glycosilated portion of the total hemoglobin increases.

Therefore, it is an object of the present invention to provide a process with which the glycosilated hemoglobin can rapidly be determined dependably and precisely by a technically simple procedure.

BRIEF DESCRIPTION

The present invention takes advantage of the surprising discovery that Haptoglobin (Hp) binds glycosilated hemoglobin more quickly than non-glycosilated hemoglobin. This difference is further enhanced by the addition of compounds which have a binding action on the allosteric effector places. To use this effect, the hemoglobin is liberated from erythrocytes by chemical or physical methods and the reaction rate of the liberated hemoglobin is followed to index the amount of glycosilated and non-glycosilated hemoglobin portions.

$I_t$ = fluorescent intensity at time t $I_\infty$ = fluorescent intensity after conclusion of the reaction.

Figure 3:
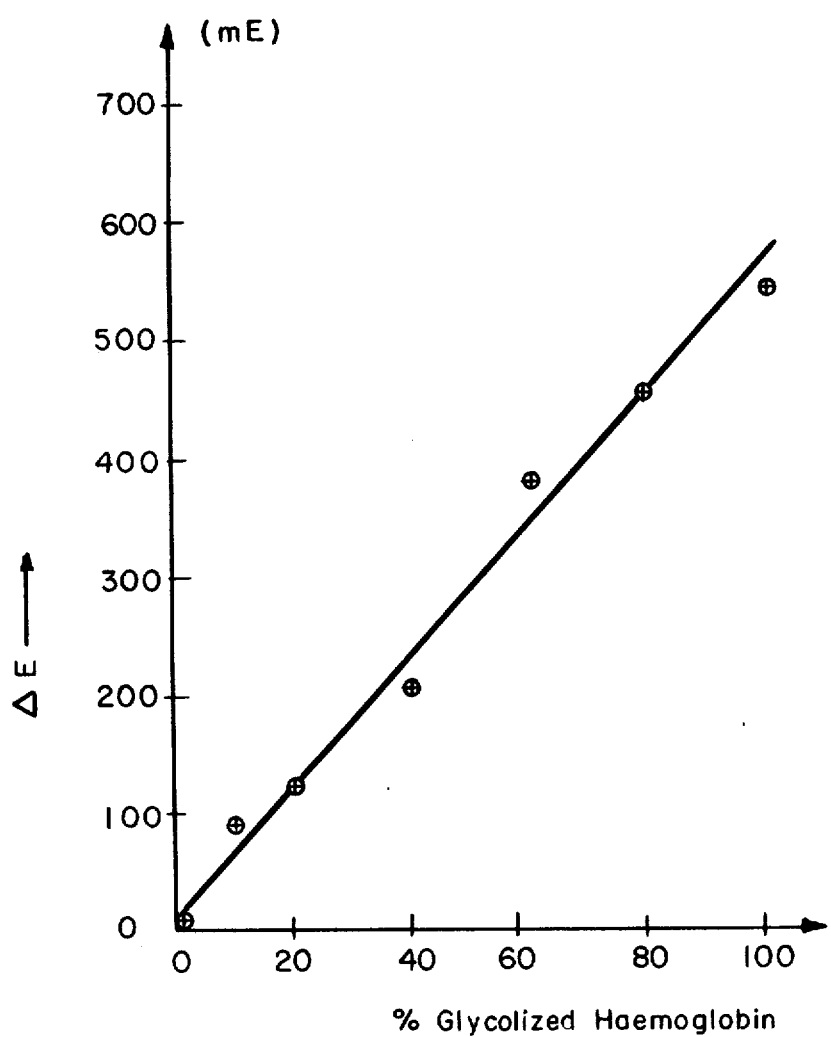

FIG. 3: dependence of the hemoglobin bound on to haptoglobin upon the percentage proportion of glycosilated hemoglobin in the total hemoglobin content.

DESCRIPTION

This problem is solved by the process according to the present invention in which, after a chemical or physical treatment of a blood sample for the liberation of the hemoglobin from the erythrocytes, a differentiation of the glycosilated and non-glycosilated hemoglobin portions is carried out with the help of haptoglobin and either the reaction between hemoglobin and haptoglobin is followed kinetically or the portion of the hemoglobin which is or is not bound to the haptoglobin is measured by known methods.

By differentiation of glycosilated and non-glycosilated hemoglobin, there are to be understood all methods which permit a differentiation of the glycosilated and non-glycosilated hemoglobin on the basis of their chemical and physical properties.

Thus, according to the present invention, there is provided a process for the determination of glycosilated hemoglobin in a blood sample in which glycosilated and non-glycosilated hemoglobin is first liberated from the erythrocytes by chemical or physical treatment, if desired, a conformational change is brought about in the hemoglobin, e.g. by conversion of the hemoglobin into methemoglobin, thereafter a differentiation of the glycosilated and non-glycosilated hemoglobin is carried out and subsequently the non-glycosilated and/or the glycosilated portion of the hemoglobin is determined in known manner, wherein the differentiation of the glycosilated and non-glycosilated hemoglobin is carried out with the help of haptoglobin.

The process according to the present invention can be carried out in the presence of an appropriate buffer system. As such buffer system can be used each buffer system effective in the pH-range of from 4.0 to 8.5 and preferably from 6.0 to 7.0. Phosphate and bis-tris buffer are especially preferred.

Haptoglobin (Hp) is a plasma protein. It has long been known that haptoglobin is able to bind hemoglobin liberated from erythrocytes (see, for example, T. Sasazuki, immunochemistry, 8, 695–704/1971).

Figure 1:
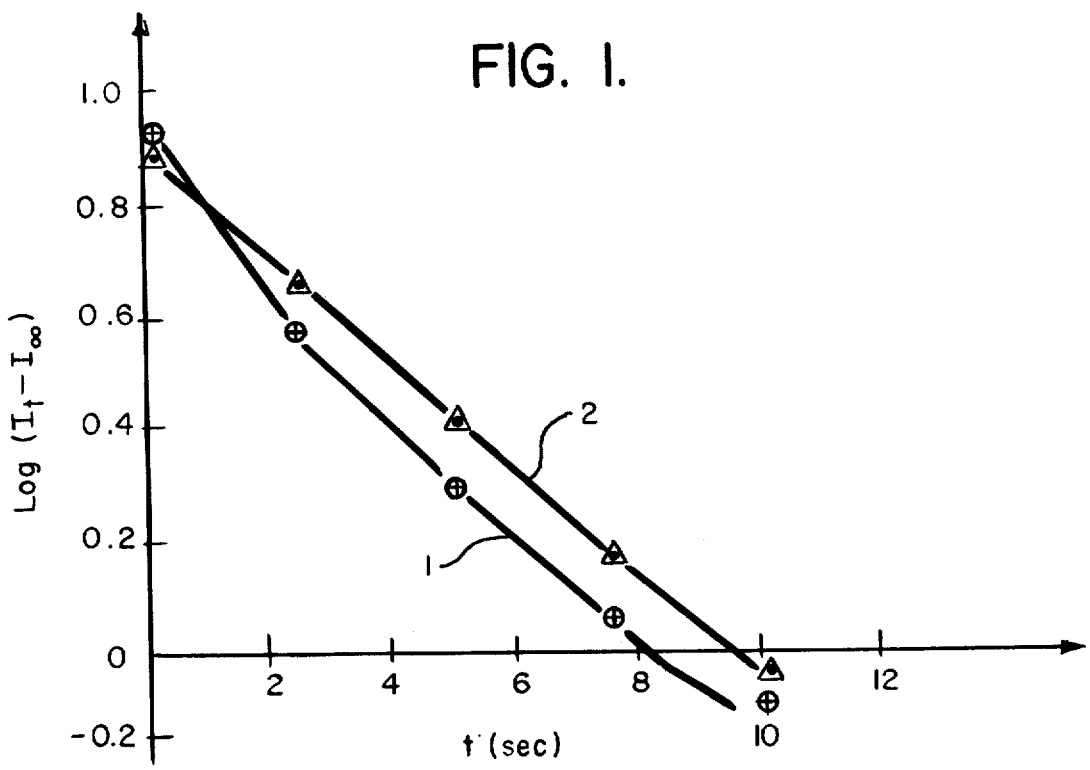
FIG. 1: decrease of the fluorescent intensity of a haptoglobin solution after the addition of glycosilated (curve 1) and non-glycosilated (curve 2) hemoglobin $I_t$ = fluorescent intensity at time t $I_\infty$ = fluorescent intensity after conclusion of the reaction

Surprisingly, we have ascertained that glycosilated and non-glycosilated hemoglobin differ with regard to their binding behaviour towards haptoglobin. Glycosilated hemoglobin is bound more quickly to haptoglobin than non-glycosilated hemoglobin. This follows, for example, from the decrease of the fluorescent intensity of a haptoglobin-containing measurement solution after the addition of glycosilated or non-glycosilated hemoglobin. The measurement of the fluorescent radiation, which represents a measure of the exchange action between hemoglobin and haptoglobin, can take place in known manner. In FIG. 1 of the accompanying drawings, there is plotted the decrease of the fluorescent intensity for both measurement solutions against time. It can be seen that the fluorescent intensity, after the addition of glycosilated hemoglobin, decreases more quickly than after the addition of non-glycosilated hemoglobin. This indicates that the binding action between haptoglobin and glycosilated hemoglobin is stronger than between haptoglobin and non-glycosilated hemoglobin.

The process for the determination of the glycosilated portion of the total hemoglobin is preferably carried out by first liberating the glycosilated and the non-glycosilated hemoglobin from the erythrocytes by conventional methods. The hemolysed blood sample is, optionally after the addition of an appropriate oxidation agent for the conversion of hemoglobin into methemoglobin, added to a haptoglobin-containing solution. The glycosilated part of the hemoglobin is preferentially bound to the haptoglobin. For the differentiation of the bound from the non-bound portion of the hemoglobin or methemoglobin, use is made of conventional measurement methods. By the measurement of different hemoglobin-containing samples with differing contents of glycosilated hemoglobin, a calibration curve can be produced on the basis of which the glycosilated portion of the total hemoglobin in unknown samples can be determined.

The difference in binding behaviour of glycosilated and non-glycosilated hemoglobin with regard to haptoglobin can be increased by the addition of one or more compounds with a binding action on the allosteric effector places. Such compounds are known. By way of example, there may be mentioned organic phosphorus compounds, such as 2,3-diphosphoglycerate and inositol hexaphosphate, organic sulphates, such as inositol hexasulphate, and carboxylic acids, such as mellitic acid.

Thus, according to a preferred embodiment of the process according to the present invention, the differentiation of the glycosilated and non-glycosilated hemoglobin is carried out with the help of haptoglobin with the addition of one or more compounds with a binding action on the allosteric effector places of the hemoglobin. For carrying out this preferred embodiment of the process according to the present invention, a number of substances with binding action on the allosteric effector places are available. According to the present invention, it is especially preferred to use inositol hexaphosphate, 2,3-diphosphoglycerate or mellitic acid. These substances with a binding action are added to the solution in at least equivalent amount, referred to the hemoglobin content. In general, however, it is of advantage to use these substances in excess and preferably in a 10 to 200 fold molar excess.

Figure 2:
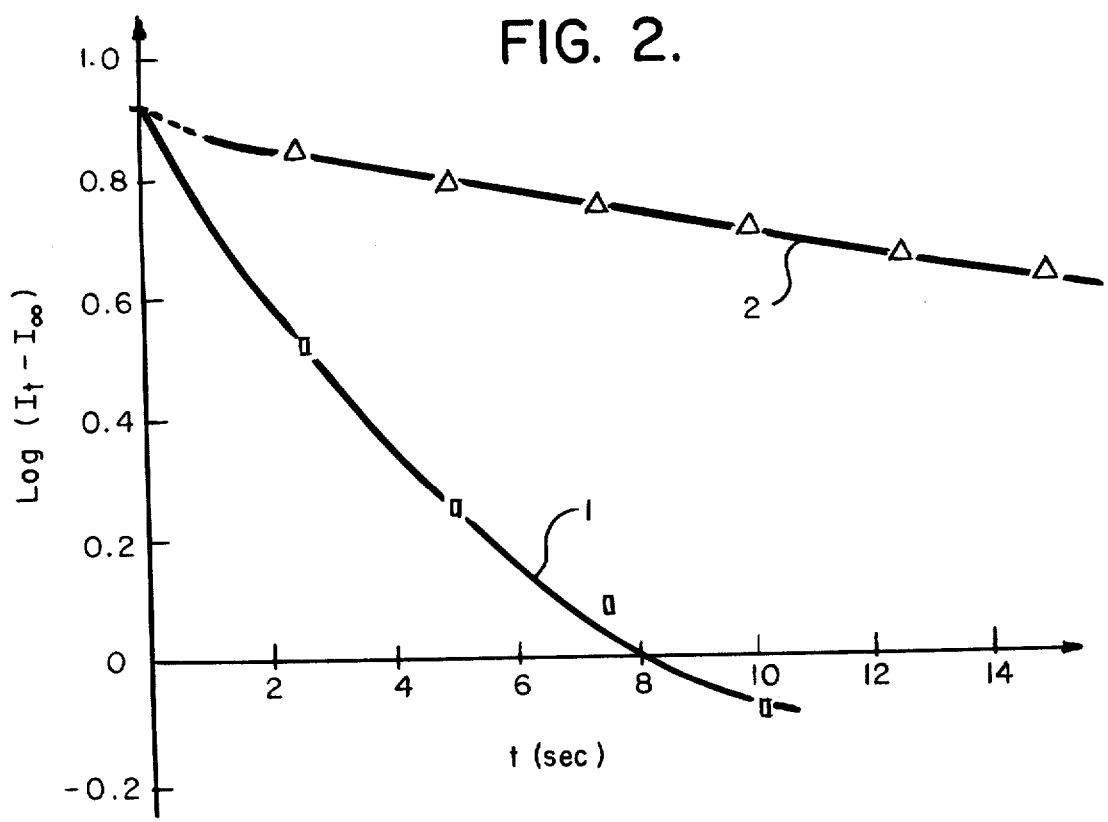
FIG. 2: decrease of the fluorescent intensity of a haptoglobin solution after the addition of glycosilated hemoglobin and inositol hexaphosphate (curve 1) and of non-glycosilated hemoglobin and inositol hexaphosphate (curve 2)

The influence of inositol hexaphosphate on the binding behaviour of glycosilated and non-glycosilated hemoglobin with regard to haptoglobin can clearly be seen from FIG. 2 of the accompanying drawings in which the decrease of the fluorescent intensity of a haptoglobin-containing solution after the addition of inositol hexaphosphate and glycosilated hemoglobin (curve 1) and of non-glycosilated harmoglobin (curve 2) is plotted against time. The course of the measurement curves clearly shows that, in the presence of inositol hexaphosphate, glycosilated hemoglobin is bound to haptoglobin considerably more quickly than the non-glycosilated hemoglobin.

Before the differentiation of glycosilated and non-glycosilated hemoglobin, it can be advantageous to convert the hemoglobin, normally present after the hemolysis of the erythrocytes, into methemoglobin. For this purpose, a number of known methods are available, for example oxidation with potassium ferricyanide or with sodium nitrite.

It is advantageous to stabilise not only the hemoglobin but possibly also the methemoglobin with one or more heme-binding ligands. In principle, all possible heme-binding ligands can be used for the process according to the present invention, alkyl isocyanides, oxygen, carbon monoxide and nitrogen monoxide being especially preferred as heme-binding ligands for hemoglobin and fluoride, azide, cyanide and water being especially preferred as heme-binding ligands for methemoglobin. The concentration of heme-binding ligands in the measurement solution must be at least equimolar to the hem concentration. Since each hemoglobin molecule contains four heme residues, the minimum concentration must correspond to four times the hemoglobin concentration. Advantageously, however, the heme-binding ligands are also used in large excess and preferably in a 10 to $10^5$ fold molar excess.

Furthermore, it is advantageous to add an agent stabilizing ion binding to the measurement solution before contacting with the haptoglobin. Examples of such agents with a stabilizing action on ionic binding include polyethylene glycols and saccharose.

Hemoglobin occurs in blood in two forms, the oxy and the deoxy form. For the process according to the present invention, it is preferable to bring the hemoglobin contained in the hemolysed blood sample into a uniform form, i.e. either into the oxy or into the deoxy form. The total hemoglobin content is preferably converted into the deoxy form before the differentiation of the glycosilated and non-glycosilated hemoglobin. Methods for the conversion of the oxy form into the deoxy form or of the deoxy into the oxy form are known. For example, the oxy form can be converted into the deoxy form with the use of a dithionite or of some other appropriate reducing agent.

Quite especially preferred is the embodiment of the process according to the present invention in which the hemoglobin contained in the hemolysed blood sample is completely converted into the deoxy form with a reducing agent, for example sodium dithionite, mixed with one or more substances with a binding action on the allosteric effector places and/or with one or more hembinding ligands and thereafter brought into contact with haptoglobin. In this way, only the glycosilated portion of the total hemoglobin content of a sample is bound by the haptoglobin and can be determined quantitatively.

The haptoglobin is used in an at least equimolar amount, referred to the hemoglobin. However, here, too, a substantial excess is of advantage, a 2 to 50 fold molar amount being preferred.

The haptoglobin can be brought into contact with the measurement solution in free form. In this case, the glycosilated portion of the total hemoglobin is preferably determined in the homogeneous phase by known methods. For example, the glycosilated portion can be measured by the fluorescent extinction method of Nagel and Gibson (J. Biol. Chem., 242, 3428/1967). Another possibility is provided by the differing pH dependence of the pseudo-peroxidase activity of free and haptoglobin-bound hemoglobin (cf. Kawamura et al., Biochim. Biophys. Acta, 285, 22–27/1972).

Since haptoglobin can be regarded as being a natural antibody for hemoglobin, other methods which can be used for the determination of the exchange action between haptoglobin and hemoglobin are all those known from immuno-diagnosis, such as radioimmunoassay, enzyme immunoassay and the like.

Furthermore, it is possible to fix the haptoglobin on to a carrier. In this case, the determination process can be carried out either by:

(a) dipping the carrier provided with haptoglobin into a hemolysed, optionally pre-treated blood sample or (b) dropping a definite amount of a pre-treated blood sample on to the haptoglobin carrier or (c) eluting the haptoglobin from the carrier with a definite amount of a pre-treated blood sample.

The carrier materials can be any of those normally used for analytical detection reagents, such as paper, cellulose, fibre fleece, porous synthetic resins and the like. The production of the carrier-bound haptoglobin takes place by dipping the carrier into or spraying with a haptoglobin-containing solution.

The haptoglobin can also be covalently bound to an insoluble carrier. The insoluble carriers can be all those carrier materials which are suitable for fixing proteins. The attachment of the haptoglobin to the carrier material takes place in known manner. The carrier-fixed haptoglobin is added to the hemolysed blood sample to which the above-mentioned additional materials have possibly also been added. After sufficient contact time, for example after about 1 minute, the insolubilized haptoglobin with the bound glycosilated portion of the hemoglobin is separated off and the glycosilated hemoglobin determined in the usual way, either directly photometrically on the basis of its inherent colour or also on the basis of its pseudo-peroxidate activity.

The haptoglobin-containing carrier can also be placed in a column through which the hemolysed blood sample, optionally provided with additives, is passed. In the case of this method, the glycosilated portion of the hemoglobin adheres to the carrier-bound haptoglobin and can thus easily be separated from the non-glycosilated portion of the hemoglobin which remains in the solution. In this case, it is preferable to determine the non-bound, non-glycosilated portion of the hemoglobin in the eluate, the $HbA_1$ content then being given by the difference between the total hemoglobin and the measured, non-glycosilated portion of the hemoglobin.

Furthermore, the present invention provides a reagent for the determination of the glycosilated hemoglobin in a blood sample, comprising an appropriate buffer system, an agent for hemolysing erythrocytes, free or carrier-bound haptoglobin and optionally one or more substances with a binding action on the allosteric effector places and/or one or more heme-binding ligands and/or one or more substances with a stabilizing action on ionic bonds.

The present invention also provides a reagent for the differentiation of glycosilated and non-glycosilated hemoglobin, which contains haptoglobin in free or carrier-bound form.

The following Examples are given for the purpose of illustrating the present invention:

EXAMPLE 1

2.2 ml. of a solution which contains 0.3 mmol/liter potassium ferricyanide, 25 mmol/liter sodium fluoride and 45.5 mg./liter haptoglobin of human origin (mixed type) in 100 mmol/liter phosphate buffer (pH 6.70) are introduced into a measurement cuvette. After the addition of 100 μl. of a 0.05% solution of glycosilated hemoglobin, which also contains 0.3 mmol/liter potassium ferricyanide and 25 mmol/liter sodium fluoride, the decrease of the fluorescent intensity is followed chronologically (excitation wavelength 280 nm, emission wavelength 330 nm). The measurement results obtained are given in FIG. 1 (curve 1).

In the same manner as described above, there is measured the course of the fluorescent intensity after non-glycosilated hemoglobin has been added to the measurement solution instead of the glycosilated hemoglobin. The results obtained are also given in FIG. 1 (curve 2).

EXAMPLE 2

Measurement solutions are prepared in the manner described in Example 1. However, instead of the phosphate buffer, use is made of a 0.05 molar bis-tris buffer (pH=6.70) [bis-tris buffer=N,N-bis-(2-hydroxyethyl)-imino-tris-(hydroxymethyl)-methane]. Before the addition of the glycosilated or of the non-glycosilated hemoglobin, the measurement solutions are, in each case, mixed with 0.2 mmol/liter inositol hexaphosphate. The chronological decrease of the fluorescent intensity is shown in FIG. 2.

EXAMPLE 3

Preparation of haptoglobin-Sepharose 20 mg. Haptoglobin of human origin (mixed type) of the firm Behringwerke AG are coupled to 4 g. cyanogen bromide-activated Sepharose according to the process of Klein and Mihaesco (Biochem. and Biophys. Research Comun., 52, 774–778/1973). The carrier-bound haptoglobin preparation obtained is diluted by the addition of 16 g. inactive Sepharose. A preparation is obtained containing haptoglobin coupled to Sepharose with a binding capacity of $5 \times 10^{-9}$ mole hemoglobin per 1 g. of moist mass.

Determination of hemoglobin bound to haptoglobin-Sepharose 1 ml. of a $8 \times 10^{-7}$ mol/liter solution of hemoglobin in 0.05 mol/liter bis-tris buffer (pH 6.70) is mixed with about 5 mg. sodium dithionite for conversion into the deoxy form. Inositol hexaphosphate and n-butyl isocyanide are successively added in the following concentrations:

| sample No. | Hemoglobin | inositol hexaphosphate (mol/l.) | n-butyl isocyanide (mol/l.) | extinction (mE) |
|---|---|---|---|---|
| 1 | $HbA_1$ | $5 \cdot 10^{-5}$ | 0 | 0 |
| 2 | $HbA_1$ | $5 \cdot 10^{-5}$ | $5 \cdot 10^{-4}$ | 188 |
| 3 | $HbA_1$ | 0 | $5 \cdot 10^{-4}$ | 194 |
| 4 | $HbA_0$ | $5 \cdot 10^{-5}$ | 0 | 0 |
| 5 | $HbA_0$ | $5 \cdot 10^{-5}$ | $5 \cdot 10^{-4}$ | 0 |
| 6 | $HbA_0$ | 0 | $5 \cdot 10^{-4}$ | 184 |

The solution is intensively mixed for 1 minute, by shaking, with 160 mg. of the haptoglobin-Sepharose preparation prepared in the above-described manner. Subsequently, it was washed once with dithionite-containing buffer and twice only with buffer and then separated off from the supernatant.

The hemoglobin bound to the haptoglobin-Sepharose is determined in known manner on the basis of its pseudo-peroxidase activity with guaiacol. For this purpose, to the centrifuged haptoglobin-Sepharose there is added 1 ml. of a 30 mmol/liter guaiacol solution in 0.1 mole/liter acetate buffer (pH 4.0). The reaction is started by the further addition of 50 μl. of a 1% hydrogen peroxide solution. After a reaction time of 5 minutes, the Sepharose is centrifuged off and the extinction of the resultant coloured material in the supernatant is measured at 436 nm. The extinction values found are given in the above Table.

The extinction values found show that, in the presence of inositol hexaphosphate alone, neither glycosilated nor non-glycosilated hemoglobin are bound by the haptoglobin-Sepharose. In the presence of n-butyl isocyanide, without the addition of inositol hexaphosphate, an exchange reaction takes place between the haptoglobin and not only the non-glycosilated but also the glycosilated hemoglobin. A differentiation between non-glycosilated and glycosilated hemoglobin is then possible with a good degree of exactitude when inositol hexaphosphate and n-butyl isocyanide are added to the sample. The extinction values obtained show that, in this case, only the glycosilated portion of the hemoglobin is bound to the haptoglobin-Sepharose.

EXAMPLE 4

1 ml of a $8 \times 10^{-7}$ mol/l solution of hemoglobin in 0.05 mol/liter bis-tris buffer (pH 6.70) is reacted with 5 mg sodium dithionite and 25 μl of a 0.1 mol/liter solution of sodium nitrite. After a reaction time of 5 minutes inositol hexaphosphate is added in the following concentrations:

| sample No. | hemoglobin | inositol hexaphosphate (mol/l.) | absorption (mE) |
|---|---|---|---|
| 1 | HbA$_1$ | 0 | 224 |
| 2 | HbA$_1$ | $5 \cdot 10^{-5}$ | 190 |
| 3 | HbA$_0$ | 0 | 219 |
| 4 | HbA$_0$ | $5 \cdot 10^{-5}$ | 16 |

The solution is intensively mixed for 1 minute, by shaking, with 160 mg. of the haptoglobin-Sepharose prepared as described in the Example 3. Subsequently, it was washed once with dithionite-containing buffer and twice only with buffer and then separated off from the supernatant.

The hemoglobin bound to the haptoglobin-Sepharose is determined in the manner discribed in Example 3. The extinction values found are given in the above table.

The extinction values found show that in the presence of inositol hexaphosphate the glycosilated hemoglobin is bound by the haptoglobin-Sepharose in a much higher degree than the non-glycosilated form.

EXAMPLE 5

Hemoglobin-containing samples are prepared in the manner described in Example 3, the proportion of glycosilated hemoglobin increasing from 0 to 100%.

The samples are, in each case, mixed with 5 mg. sodium dithionite, $5 \times 10^{-5}$ mole/liter inositol hexaphosphate and $5 \times 10^{-4}$ mole/liter n-butyl isocyanide and further treated as described in Example 3. The haptoglobin reagent used is a haptoglobin-Sepharose preparation obtained in a manner analogous to that described in Example 3 but which has a binding capacity of $1.7 \times 10^{-8}$ mole hemoglobin per 1 g. of preparation. In FIG. 3, the extinction values found are plotted in dependence upon the percentage proportion of glycosilated hemoglobin in the total hemoglobin content.

With the help of the standard curve reproduced in FIG. 3, there can be determined the unknown content of glycosilated hemoglobin in a sample according to the process here described.

It will be understood that the specification and examples are illustrative but not limitative of the present invention and that other embodiments within the spirit and scope of the invention will suggest themselves to those skilled in the art.

What is claimed is:

1. A process for the determination of glycosilated hemoglobin in a blood sample containing hemoglobin comprised of both glycosilated and non-glycosilated hemoglobin comprising the steps
    liberating the glycosilated and non-glycosilated hemoglobin from erythrocytes in the blood sample, and
    differentiating the glycosilated and non-glycosilated hemoglobin by reaction with haptoglobin, and
    determining the glycosilated and/or the non-glycosilated portion of the hemoglobin.

2. The process of claim 1 wherein the hemoglobin is converted to methemoglobin before reacting with haptoglobin.

3. The process of claim 1, wherein the differentiation of glycosilated and non-glycosilated hemoglobin is accomplished in the presence of buffer system.

4. The process of claim 1, wherein the differentiation of glycosilated and non-glycosilated hemoglobin is accomplished in the presence of one or more substances which bring about a conformation change in the hemoglobin.

5. The process according to claim 4, wherein the substances which bring about a conformation change in the hemoglobin are either compounds with a binding action on the allosteric effector places or heme-binding ligands.

6. The process according to claim 5, wherein the compound with a binding action on the allosteric effector places is inositol hexaphosphate, 2,3-diphosphoglycerate or mellitic acid.

7. The process according to claim 5, wherein the heme-binding ligand is an alkyl isocyanide, oxygen, carbon monoxide or nitrogen monoxide.

8. The process of claim 2 wherein the differentiation of glycosilated and non-glycosilated hemoglobin is accomplished in the presence of one or more substances which bring about conformational change in the hemoglobin.

9. The process of claim 8 wherein the substance for effecting conformational change is a fluoride, azide, cyanide or water.

10. The process of claim 1 wherein a 2 to 50 fold excess of the amount of haptoglobin necessary to react with the hemoglobin, is used.

11. Reagent for the determination of glycosilated hemoglobin in a blood sample, comprising a chemical agent for hemolysing erythrocytes, a buffer system effective in the pH range of from 4.0 to 8.5, and free or carrier-bound haptoglobin.

12. Reagent of claim 11 further comprising one or more substances with a binding action on the allosteric effector on places of the hemoglobin and one or more heme-binding ligands and/or one or more substances with a stabilizing action on ionic bonds.

* * * * *